United States Patent [19]

Acker et al.

[11] Patent Number: 4,496,563
[45] Date of Patent: Jan. 29, 1985

[54] FUNGICIDAL THIADIAZINONES

[75] Inventors: Rolf-Dieter Acker, Leimen; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 524,202

[22] Filed: Aug. 18, 1983

[30] Foreign Application Priority Data

Aug. 20, 1982 [DE] Fed. Rep. of Germany ....... 3230923

[51] Int. Cl.³ .................. C07D 285/16; A61K 31/54; A01N 43/88
[52] U.S. Cl. ........................................ 514/222; 544/8
[58] Field of Search ............................. 544/8; 424/246

[56] References Cited

FOREIGN PATENT DOCUMENTS 54005991 3/1982 Japan .

OTHER PUBLICATIONS

Chemical Week, Jun. 21, 1972, p. 46.
Central Patents Index Basic Abstracts Journal, Section C: AGDOC, B08, 18, Apr. 1979, Seite 35, Nr. 14890B/08, Derwent Publications Ltd., London, GB. & JP.-A-54 005 991 (Nippon Soda K.K.), 01.17.1979.

Primary Examiner—John M. Ford
Attorney, Agent, or Firm—Keil & Weinkauf

[57] ABSTRACT

Thiadiazinones of the formula

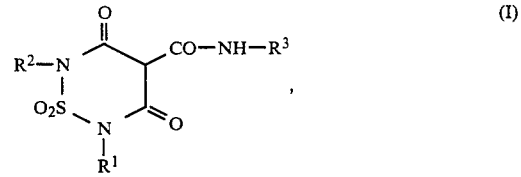

where $R^1$ and $R^2$ are identical or different and are each hydrogen, alkyl, cycloalkyl, phenyl or substituted aryl and $R^3$ is phenyl or haloalkyl-substituted, alkyl-substituted, alkoxy-substituted or haloalkoxy-substituted or alkyl- or halo-substituted phenyl, are used in fungicides.

4 Claims, No Drawings

FUNGICIDAL THIADIAZINONES

The present invention relates to thiadiazinones, processes for their preparation, fungicides containing these compounds as active ingredients and a method of controlling undesirable fungal attack with these active ingredients.

Thiadiazinones, eg. 2,6-dimethyl-4-(N-ethylcarbamyl)-3,5-dioxo-2H-3,4,5,6-tetrahydro-1,2,6-thiadiazine 1,1-dioxide, are known as insecticides and miticides (Japanese Preliminary Published Application J No. 54005-991). It is also known that N-trichloromethyl-thiotetrahydrophthalimide can be used as a fungicide (Chemical Week, 21st June 1972, page 46).

We have found that thiadiazinones of the formula $$
\begin{array}{c}
\text{R}^2-\text{N} \\
| \\
\text{O}_2\text{S}
\end{array}
\begin{array}{c}
\text{O} \\
\parallel \\
\\
\text{N} \\
| \\
\text{R}^1
\end{array}
\begin{array}{c}
\text{CO}-\text{NH}-\text{R}^3 \\
\\
\text{O}
\end{array}
\quad (I)
$$

where $R^1$ and $R^2$ are identical or different and are each hydrogen, $C_1$-$C_{10}$-alkyl, $C_3$-$C_8$-cycloalkyl, phenyl or substituted aryl and $R^3$ is phenyl or haloalkyl-substituted, alkyl-substituted, alkoxy-substituted or haloalkoxy-substituted or alkyl- and halo-substituted phenyl, have a good fungicidal action.

Because of keto-enol tautomerism, compounds of the formula I can also occur in the forms $$
\text{(Ia)}
$$

$$
\text{(Ib)}
$$

The formation of salts is also possible here.

The present invention relates both to the compounds I, Ia and Ib and to their mixtures and salts (sodium and potassium salts).

Examples of $C_1$-$C_{10}$-alkyl are methyl, ethyl, n-propyl, isopropyl, n-butyl, isobutyl, sec.-butyl, n-pentyl, isooctyl and n-decyl, examples of $C_3$-$C_8$-cycloalkyl are cyclopropyl, cyclobutyl, cyclopentyl, cyclohexyl and cyclooctyl, examples of substituted aryl are phenyl radicals which are substituted by halogen, eg. fluorine, chlorine, bromine or iodine, alkoxy, eg. methoxy, alkyl, eg. methyl, haloalkyl, eg. trifluoromethyl, or haloalkoxy, eg. trifluoromethoxy, examples of haloalkyl-substituted phenyl are phenyl radicals which are substituted by haloalkyl, eg. fluoro-, chloro- or bromo-alkyl, of 1 to 4 carbon atoms, eg. chloromethyl, chloroethyl, trifluoromethyl or pentafluoroethyl, examples of alkyl-substituted phenyl are phenyl radicals which are substituted by alkyl of 1 to 4 carbon atoms, eg. methyl, ethyl, isopropyl and prim.-, sec.- and tert.-butyl, examples of alkoxy-substituted phenyl are phenyl radicals which are substituted by alkoxy of 1 to 4 carbon atoms, eg. methoxy, ethoxy, isopropoxy and tert.-butoxy, examples of haloalkoxy-substituted phenyl are phenyl radicals which are substituted by haloalkoxy, eg. fluoro-, chloro- or bromo-alkoxy, of 1 to 4 carbon atoms, eg. trifluoromethoxy and pentafluoroethoxy, and examples of alkyl- and halo-substituted phenyl are phenyl radicals which are substituted at the same time by halogen, eg. fluorine, chlorine or bromine, and alkyl of 1 to 4 carbon atoms, eg. 2-chloro-4-methylphenyl, 4-fluoro-3-ethylphenyl and 4-bromo-2-methylphenyl.

The novel thiadiazinones of the formula I are obtained by a process wherein thiadiazinones of the formula $$
\begin{array}{c}
\text{R}^2-\text{N} \\
| \\
\text{O}_2\text{S}
\end{array}
\begin{array}{c}
\text{O} \\
\parallel \\
\\
\text{N} \\
| \\
\text{R}^1
\end{array}
\text{O},
\quad (II)
$$

where $R^1$ and $R^2$ have the above meanings, are reacted with an isocyanate of the formula $$R^3-\text{NCO} \quad (III)$$

in an inert solvent in the presence or absence of a base.

The reaction is carried out, for example, at from 25° to 200° C., preferably from 50° to 150° C. The reaction time is, for example, from 0.5 to 12 hours. Components II and III are employed, for example, in a molar ratio of from 1:1 to 1:10 (II:III), and from 0.1 to 1.0 mole of a base per mole of the compound of the formula II can be added to accelerate the reaction.

Suitable basic catalysts include tertiary amines, alkaline earth metal compounds, ammonium compounds and alkali metal compounds, and appropriate mixtures. Zinc compounds can also be used. Examples are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

Apart from the above inorganic bases, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethyleneglycolate, sodium propylene-1,2-glycolate, sodium propylene-1,3-glycolate, sodium diethylene-glycolate, sodium triethylene-glycolate, sodium dipropylene-1,2-glycolate, potassium methylate, potassium ethylate, potassium n-propylate, potassium isopropylate, potassium n-butylate, potassium isobutylate, potassium sec.-butylate, potassium tert.-butylate, potassium methyleneglycolate, potassium propylene-1,2-glycolate, potassium propylene-1,3-glycolate, potassium diethyleneglycolate, potassium triethylene-glycolate and potassium dipropylene-1,2-glycolate, for example, are also suitable.

Examples of suitable solvents are halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, p- or m-dichlorobenzene, o-, p- or m-dibromobenzene, o-, m- or p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and β,β'-dichlorodiethyl ether; nitrohydrocarbons, eg. nitromethane, nitroethane, nitrobenzene, o-, m- or p-chloronitrobenzene and o-nitrotoluene; nitriles, eg. acetonitrile, butyronitrile, isobutyronitrile, benzonitrile and m-chlorobenzonitrile; aliphatic, cycloaliphatic or aromatic hydrocarbons, eg. heptane, pinane, nonane, o-, m- or p-cymene, gasoline fractions within a boiling point range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane, octane, toluene, o-, m- or p-xylene and tetralin; esters, eg. ethyl acetate, ethyl acetoacetate and isobutyl acetate; amides, eg. formamide, methylformamide and dimethylformamide; ketones, eg. acetone and methyl ethyl ketone; sulfoxides, eg. dimethylsulfoxide; heteroaromatics, eg. pyridine, α-,β- or γ-picoline and pyrimidine; water or alcohols, eg. methanol, ethanol and isopropanol; and appropriate mixtures. The solvent is advantageously used in an amount of from 100 to 2,000% by weight, preferably from 200 to 700% by weight, based on the starting substance II.

The process can be carried out continuously or batchwise under superatmospheric or, preferably, for simplicity, atmospheric pressure.

The compounds of the formula I can be separated off and the reaction finished, for example, as follows: either the volatile constituents of the reaction mixture are distilled off under reduced pressure and the crude products of the formula I remaining as the residue are recrystallized or, where relevant, chromatographed, or, preferably, if relatively large amounts of base are used in the reaction, the reaction mixture is poured into an aqueous solution, which may or may not be cooled or diluted, of a mineral acid, eg. hydrochloric acid or sulfuric acid, and the precipitate formed is recrystallized, or the organic phase is separated off and then concentrated. Further purification can be carried out in a conventional manner, for example by recrystallization or chromatography.

METHOD 1

38.9 parts by weight of methylamidosulfonyl chloride were added a little at a time to a mixture of 17.7 parts of isopropylamine, 33.3 parts of triethylamine and 120 parts of tetrahydrofuran (THF), which was kept at from −70° to −65° C. The mixture was stirred at 20° C. for 3 hours, the insoluble material was filtered off and the solution was evaporated to dryness. The residue on the filter was extracted by stirring with methylene chloride, the mixture was filtered and the solution was concentrated. 30.6 parts of N-methyl-N'-isopropylsulfamide of melting point 50°–52° C. (starting substance) were obtained.

METHOD 2

29.5 parts of isopropylamine and 55.6 parts of triethylamine were introduced into 320 parts of THF. 60 parts of trimethylchlorosilane were added a little at a time at from 0° to −5° C. under nitrogen and the mixture was stirred at room temperature for 30 minutes and at 60° C. for 1 hour and then cooled to −10° C. 33.8 parts of sulfuryl chloride were added a little at a time and the mixture was allowed to warm to room temperature and was then stirred for 2 hours. The trimethylchlorosilane and the solvent were distilled off and the residue was washed with ice-water. 30.5 parts of N,N'-diisopropylsulfamide of melting point 98°–101° C. (starting substance) were obtained.

METHOD 3

22 parts of N-methyl-N'-isopropylsulfamide and 20.4 parts of malonyl chloride were stirred in 350 parts of toluene at 50° C. for 30 minutes and at 70° C. for 14 hours. After cooling, the solution was decanted off from the oil and the solvent was distilled off from the solution. 24 parts of 2-methyl-6-isopropyl-3,5-dioxo-2H-3,4,5,6-tetrahydro-1,2,6-thiadiazine 1,1-dioxide of $n_D^{22}$ 1.4906 (starting substance) were obtained.

EXAMPLE 1

8.8 parts by weight of 2-methyl-6-isopropyl-3,5-dioxo-2H-3,4,5,6-tetrahydro-1,2,6-thiadiazine 1,1-dioxide, 6.0 parts of phenyl isocyanate and 80 parts of pyridine were stirred at 22° C. for 30 minutes and under reflux for 3 hours. After cooling, the solution was stirred into ice-water/hydrochloric acid and the mixture was extracted twice by shaking with methylene chloride. The organic phase was dried and concentrated and the residue was recrystallized from ethanol. 13 parts of 2-methyl-4-(N-phenylcarbamyl)-6-isopropyl-3,5-dioxo-2H-3,4,5,6-tetrahydro-1,2,6-thiadiazine 1,1-dioxide of melting point 118°–120° C. (Compound No. 7) were obtained.

EXAMPLE 2

10 parts of isobutyl-3,5-dioxo-2H-3,4,5,6-tetrahydro-1,2,6-thiadiazine 1,1-dioxide, 5.1 parts of phenyl isocyanate and 70 parts of pyridine were stirred under reflux for 3 hours. The mixture was stirred into ice-water/hydrochloric acid, brought to pH 2 and left to stand for 30 minutes and the residue was filtered off with suction and recrystallized from ethanol. 4.5 parts of 2-isobutyl-4-(N-phenylcarbamyl)-6H-3,5-dioxo-2H-3,4,5,6-tetrahydro-1,2,6-thiadiazine 1,1-dioxide of melting point 82°–84° C. (Compound No. 17) were obtained.

EXAMPLE 3

7.3 parts of 2,6-dimethyl-3,5-dioxo-2H-3,4,5,6-tetrahydro-1,2,6-thiadiazine 1,1-dioxide, 6.8 parts of phenyl isocyanate, 1.6 parts of triethylamine and 65 parts of toluene were stirred under reflux for 7 hours. The mixture was cooled, the solvent was distilled off and the crystalline residue which remained was recrystallized from ethanol. 9.1 parts of 2,6-dimethyl-4-(N-phenylcarbamyl)-3,5-dioxo-2H-3,4,5,6-tetrahydro-1,2,6-thiadiazine 1,1-dioxide of melting point 151°–153° C. (Compound No. 1) were obtained.

Those compounds of the formula I in Table 1 which follows for which melting points (m.p.) are given were prepared in a similar manner. Their structure was confirmed by IR and NMR spectroscopy and by elemental analysis. Compounds for which there are no physical chemistry data can be obtained in the same way as the compounds actually prepared; on the basis of their similar structure, it can be expected that they have similar actions to the compounds investigated in more detail.

| No. | $R^1$ | $R^2$ | $R^3$ | M.p. [°C.] |
|---|---|---|---|---|
| 1 | $CH_3$ | $CH_3$ | $C_6H_5$ | 151–153 |
| 2 | $CH_3$ | $C_2H_5$ | $C_6H_5$ | |
| 3 | $C_2H_5$ | $C_2H_5$ | $C_6H_5$ | 116–118 |
| 4 | $CH_3$ | n-$C_3H_7$ | $C_6H_5$ | 114–116 |
| 5 | $C_2H_5$ | n-$C_3H_7$ | $C_6H_5$ | |
| 6 | n-$C_3H_7$ | n-$C_3H_7$ | $C_6H_5$ | 72–74 |
| 7 | $CH_3$ | i-$C_3H_7$ | $C_6H_5$ | 118–120 |
| 8 | $C_2H_5$ | i-$C_3H_7$ | $C_6H_5$ | |
| 9 | n-$C_3H_7$ | i-$C_3H_7$ | $C_6H_5$ | |
| 10 | i-$C_3H_7$ | i-$C_3H_7$ | $C_6H_5$ | 82–84 |
| 11 | i-$C_3H_7$ | i-$C_3H_7$ | $C_6H_5$ (Na salt) | |
| 12 | $CH_3$ | n-$C_4H_9$ | $C_6H_5$ | 120–123 |
| 13 | $CH_3$ | n-$C_4H_9$ | $C_6H_5$ (Na salt) | 235 |
| 14 | $C_2H_5$ | n-$C_4H_9$ | $C_6H_5$ | |
| 15 | i-$C_3H_7$ | n-$C_4H_9$ | $C_6H_5$ | |
| 16 | n-$C_4H_9$ | n-$C_4H_9$ | $C_6H_5$ | |
| 17 | H | i-$C_4H_9$ | $C_6H_5$ | 82–84 |
| 18 | $CH_3$ | i-$C_4H_9$ | $C_6H_5$ | |
| 19 | $C_2H_5$ | i-$C_4H_9$ | $C_6H_5$ | |
| 20 | n-$C_3H_7$ | i-$C_4H_9$ | $C_6H_5$ | |
| 21 | i-$C_3H_7$ | i-$C_4H_9$ | $C_6H_5$ | |
| 22 | n-$C_4H_9$ | i-$C_4H_9$ | $C_6H_5$ | |
| 23 | i-$C_4H_9$ | i-$C_4H_9$ | $C_6H_5$ | |
| 24 | $CH_3$ | t-$C_4H_9$ | $C_6H_5$ | |
| 25 | $CH_3$ | cyclopropyl | $C_6H_5$ | |
| 26 | i-$C_3H_7$ | cyclopropyl | $C_6H_5$ | |
| 27 | $CH_3$ | cyclobutyl | $C_6H_5$ | |
| 28 | i-$C_3H_7$ | cyclobutyl | $C_6H_5$ | |
| 29 | $CH_3$ | cyclopentyl | $C_6H_5$ | |
| 30 | n-$C_3H_7$ | cyclopentyl | $C_6H_5$ | |
| 31 | i-$C_3H_7$ | cyclopentyl | $C_6H_5$ | |
| 32 | cyclopentyl | cyclopentyl | $C_6H_5$ | |
| 33 | cyclobutyl | cyclobutyl | $C_6H_5$ | |
| 34 | cyclopropyl | cyclopropyl | $C_6H_5$ | |
| 35 | $CH_3$ | cyclohexyl | $C_6H_5$ | |
| 36 | $C_2H_5$ | cyclohexyl | $C_6H_5$ | |
| 37 | i-$C_3H_7$ | cyclohexyl | $C_6H_5$ | |
| 38 | cyclohexyl | cyclohexyl | $C_6H_5$ | 103–106 |
| 39 | cyclohexyl | cyclohexyl | $C_6H_5$ (Na salt) | 240 |
| 40 | $CH_3$ | $C_6H_5$ | $C_6H_5$ | |
| 41 | $C_2H_5$ | $C_6H_5$ | $C_6H_5$ | |
| 42 | n-$C_3H_7$ | $C_6H_5$ | $C_6H_5$ | |
| 43 | i-$C_3H_7$ | $C_6H_5$ | $C_6H_5$ | |
| 44 | i-$C_4H_9$ | $C_6H_5$ | $C_6H_5$ | |
| 45 | $CH_3$ | 4-Cl—$C_6H_4$ | $C_6H_5$ | 165–167 |
| 46 | i-$C_3H_7$ | 4-Cl—$C_6H_4$ | $C_6H_5$ | |
| 47 | $CH_3$ | 4-$CH_3$—$C_6H_4$ | $C_6H_5$ | |
| 48 | n-$C_3H_7$ | 4-$CH_3$—$C_6H_4$ | $C_6H_5$ | |
| 49 | $CH_3$ | 4-$CH_3O$—$C_6H_4$ | $C_6H_5$ | |
| 49 | $CH_3$ | 4-$CH_3O$—$C_6H_4$ | $C_6H_5$ | |
| 50 | $CH_3$ | 3-$CF_3O$—$C_6H_4$ | $C_6H_5$ | |
| 51 | $CH_3$ | 3-$CH_3$—$C_6H_4$ | $C_6H_5$ | |
| 52 | $CH_3$ | 3-$CH_3O$—$C_6H_4$ | $C_6H_5$ | |
| 53 | $CH_3$ | $CH_3$ | 4-$CH_3$—$C_6H_4$ | |
| 54 | $C_2H_5$ | $CH_3$ | 3-$CH_5$—$C_6H_4$ | |
| 55 | i-$C_3H_7$ | i-$C_3H_7$ | 2-$CH_3$—$C_6H_4$ | |
| 56 | $CH_3$ | $CH_3$ | 4-$CF_3$—$C_6H_4$ | 144–145 |
| 57 | $CH_3$ | i-$C_3H_7$ | 4-$CF_3$—$C_6H_4$ | |
| 58 | i-$C_3H_7$ | i-$C_3H_7$ | 4-$CF_3$—$C_6H_4$ | |
| 59 | $CH_3$ | $CH_3$ | 3-$CF_3$—$C_6H_4$ | |
| 60 | $CH_3$ | n-$C_4H_9$ | 3-$CF_3$—$C_6H_4$ | |
| 61 | i-$C_3H_7$ | i-$C_3H_7$ | 3-$CF_3$—$C_6H_4$ viscous | |
| 62 | $CH_3$ | $CH_3$ | 4-$CH_3O$—$C_6H_4$ | |
| 63 | $CH_3$ | i-$C_3H_7$ | 4-$CH_3O$—$C_6H_4$ | |
| 64 | i-$C_3H_7$ | i-$C_3H_7$ | 4-$CH_3O$—$C_6H_4$ | |
| 65 | $CH_3$ | $CH_3$ | 3-$CH_3O$—$C_6H_4$ | |
| 66 | $CH_3$ | $CH_3$ | 4-$CF_3O$—$C_6H_4$ | |
| 67 | i-$C_3H_7$ | i-$C_3H_7$ | 3-$CF_3O$—$C_6H_4$ | |
| 68 | $CH_3$ | $CH_3$ | 3-$CH_3$—4-Cl—$C_6H_3$ | |
| 69 | $C_2H_5$ | $C_2H_5$ | 2-$CH_3$—4-Cl—$C_6H_3$ | |
| 70 | i-$C_3H_7$ | i-$C_3H_7$ | 2-$CH_3$—4-Cl—$C_6H_3$ | 119–121 |
| 71 | $CH_3$ | $CH_3$ | 2-$CH_3$—5-Cl—$C_6H_3$ | |

The novel active ingredients have a strong fungitoxic action on phytopathogenic fungi, especially from the Phycomycetes class. The novel compounds are therefore suitable for instance for combating *Phytophthora infestans* in tomatoes and potatoes, *Phytophthora parasitica* in strawberries, *Phytophthora cactorum* in apples, *Pseudoperonospora cubensis* in cucumbers, *Pseudoperonospora humuli* in hops, *Peronospora destructor* in onions, *Peronospora sparsa* in roses, *Peronospora tabacina* in tobacco, *Plasmopara viticola* in grapes, *Plasmopara halstedii* in sunflowers, *Sclerospora macrospora* in Indian corn, *Bremia lactucae* in lettuce, *Mucor mucedo* in fruit, and *Rhizopus nigricans* in beets. The active ingredients also have an advantageous bactericidal action on, for instance, *Staphylococcus aureus, Escheria coli,* and Xanthomonas and Pseudomonas species. The fungicidal agents contain from 0.1 to 95, and preferably from 0.5 to 90, wt% of active ingredient. The application rates depend on the type of effect desired, and range from 0.1 to 5 kg of active ingredient per hectare. Some of the active ingredients also have curative properties, i.e., the agents may be applied after infection of the plants by the pathogen and success is still ensured.

The novel active ingredients may also be mixed and applied with other active ingredients, e.g., herbicides, insecticides, growth regulators, fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together. The spectrum of action is particularly favorably influenced when the compounds according to the invention are mixed with the following fungicides:
sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylpropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylamino-benzimidazole
2-[furyl-(2)]-benzimidazole
2-[triazolyl-(4)]-benzimidazole
N-(1,1,2,2-tetrachloroethylthio)-tetrahydrophthalimide
N-trichloromethylthio-tetrahydrophthalimide
N-trichloromethyl-phthalimide
N-dichlorofluoromethylthio-N',N'-dimethyl-N-phenyl-sulfuric acid diamide
5-ethoxy-3-trichlorommethyl-1,2,3-thiadiazole
2-thiocyanomethylthiobenzthiazole
1,4-dichloro-2,5-dimethoxybenzene
4-(2-chlorophenylhydrazono)-3-methyl-5-isooxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic acid anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichloroethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethyl-morpholine
N-[3-(p-tert.-butylphenyl)-2-methylpropyl]-piperidine
1-[2-(2,4-dichlorophenyl)-4-ethyl-1,3-dioxolan-2-yl-ethyl]-1H-1,2,4-triazole
1-[2-(2,4-dichlorophenyl)-4-n-propyl-1,3-dioxolan-2-yl-ethyl]-1H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidine-methanol
5-butyl-2-dimethylamino-4-hydroxy-6-methyl-pyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-amino-butyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropylcarbamoylhydantoin
N-(3,5-dichlorophenyl)-1,2-dimethylcyclopropane-1,2-dicarboxylic acid imide.

The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of such formulations follow.

I. 10 parts by weight of compound no. 4 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil. By pouring the solution into water, an aqueous dispersion is obtained.

II. 20 parts by weight of compound no. 6 is dissolved in a mixture consisting of 60 parts by weight of cyclohexanone, 30 parts by weight of isobutanol, and 10 parts by weight of the adduct of 40 moles of ethylene oxide and 1 mole of castor oil. By pouring the solution into water and finely distributing it therein, an aqueous dispersion is obtained.

III. 20 parts by weight of compound no. 7 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and finely distributing it therein, an aqueous dispersion is obtained.

IV. 80 parts by weight of compound no. 13 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By finely distributing the mixture in water, a spray liquor is obtained.

V. 3 parts by weight of compound no. 45 is intimately mixed with 97 parts by weight of particulate kaolin. A dust is obtained containing 3% by weight of the active ingredient.

VI. 30 parts by weight of compound no. 56 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VII. 40 parts by weight of compound no. 4 is intimately mixed with 10 parts of the sodium salt of a phenolsulfonic acid-urea-formaldehyde condensate, 2 parts of silica gel and 48 parts of water to give a stable aqueous dispersion.

VIII. 20 parts of compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may also be successfully employed in the ultra-low-volume method (ULV), where it is possible to apply formulations containing more than 95 wt% of active ingredients, or 100% active ingredient (without any additives).

For the experiments described below, the following prior art compounds were used for comparison purposes:

2,6-dimethyl-4-(N-ethylcarbamoyl)-3,5-dioxo-2H-3,4,5,6-tetrahydro-1,2,6-thiadiazine-1,1-dioxide (A);
N-trichloromethylthio-tetrahydrophthalimide (B).

EXPERIMENT 1

Action of *Phytophthora infestans* in tomatoes

Leaves of potted tomatoes of the "Groesse Fleischtomate" variety were sprayed with aqueous liquors containing (dry basis) 80% of active ingredient and 20% of emulsifier. After the sprayed-on layer had dried, the leaves were infected with a zoospore suspension of *Phytophthora infestans*. The plants were then placed for 5 days in a steam-saturated chamber kept at 16° to 18° C. After this period, the disease had spread on the untreated control plants to such an extent that the fungicidal action of the compounds was able to be assessed.

The results of this experiment show that for example compounds nos. 4, 6, 7, 13, 45 and 56, applied as 0.025 wt% sprays, had a better fungicidal action (e.g., 97%) than prior art compounds A and B (e.g., 60%). Compound A is strongly phytotoxic and kills tomato plants.

EXPERIMENT 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a water vapor-saturated chamber at 24° C., and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that for instance compounds nos. 4, 10 and 56, applied as 0.025 wt% sprays, had a good fungicidal action (e.g., 97%).

We claim:

1. A fungicidal composition comprising a liquid or solid carrier and a fungicidally effective amount of a thiadiazinone of the formula:

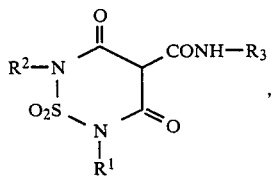

where $R^1$ and $R^2$ are identical or different and are each hydrogen, $C_1$–$C_{10}$-alkyl, $C_3$–$C_8$-cycloalkyl, phenyl or substituted phenyl and $R^3$ is phenyl or haloalkyl-substituted, alkyl-substituted, alkoxy-substituted, haloalkoxy-substituted or alkyl- and halo-substituted phenyl.

2. A process for combating fungi which comprises treating the fungi or the areas, plants or seed to be protected against fungus attack with an effective amount of a thiadiazinone of the formula:

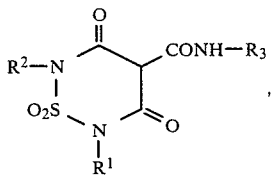

where $R^1$ and $R^2$ are identical of different and are each hydrogen, $C_1$–$C_{10}$-alkyl, $C_3$–$C_8$-cycloalkyl, phenyl or substituted phenyl and $R^3$ is phenyl or haloalkyl-substituted, alkyl-substituted, alkoxy-substituted, haloalkoxy-substituted or alkyl- and halo-substituted phenyl.

3. A fungicidal composition as defined in claim 1, wherein in the compound of the formula I, $R^1$ is alkyl of 1 to 4 carbon atoms, $R^2$ is alkyl of from 1 to 4 carbon atoms or halophenyl, and $R^3$ is phenyl or trifluoromethylphenyl.

4. A process for combating fungi as defined in claim 2, wherein in the compound of the formula I, $R^1$ is alkyl of 1 to 4 carbon atoms, $R^2$ is alkyl of from 1 to 4 carbon atoms or halophenyl, and $R^3$ is phenyl or trifluoromethylphenyl.

* * * * *